(12) United States Patent
Permuy et al.

(10) Patent No.: US 7,958,772 B2
(45) Date of Patent: Jun. 14, 2011

(54) DENSITY AND VISCOSITY SENSOR

(75) Inventors: Alfred Permuy, Rueil Malmaison (FR); Eric Donzier, Bercheres sur Vesgre (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/817,404

(22) PCT Filed: Feb. 24, 2006

(86) PCT No.: PCT/EP2006/001886
§ 371 (c)(1),
(2), (4) Date: Sep. 18, 2007

(87) PCT Pub. No.: WO2006/094694
PCT Pub. Date: Sep. 14, 2006

(65) Prior Publication Data
US 2008/0156093 A1 Jul. 3, 2008

(30) Foreign Application Priority Data
Mar. 4, 2005 (EP) .................................. 05290502

(51) Int. Cl.
*G01N 11/16* (2006.01)
*G01N 9/34* (2006.01)
(52) U.S. Cl. ...................... 73/54.25; 73/32 A
(58) Field of Classification Search ............ 73/32 A, 73/54.41
See application file for complete search history.

(56) References Cited

U.S. PATENT DOCUMENTS
4,922,745 A * 5/1990 Rudkin et al. .............. 73/32 A
5,323,638 A * 6/1994 Langdon ..................... 73/32 A FOREIGN PATENT DOCUMENTS
EP 0 282 251 9/1988
WO WO 02/077613 10/2002
WO WO 2004/086002 10/2004

* cited by examiner

*Primary Examiner* — Hezron Williams
*Assistant Examiner* — Paul West (57) ABSTRACT

A density and viscosity sensor 1 for measuring density and viscosity of fluid F, the sensor 1 comprising a resonating element 3, 3A, 3B, 3C, 3D arranged to be immersed in the fluid F, an actuating/detecting element 4A, 4B coupled to the resonating element, and a connector 7 for coupling to the actuating/detecting element 4A, 4B. The sensor 1 further comprises a housing 2 defining a chamber 8A isolated from the fluid F, the housing 2 comprising an area of reduced thickness defining a membrane 9 separating the chamber 8A from the fluid F. The actuating/detecting element 4A, 4B is positioned within the chamber so as to be isolated from the fluid F and mechanically coupled to the membrane 9. The resonating element 3, 3A, 3B, 3C, 3D arranged to be immersed in the fluid F is mechanically coupled to the membrane 9. The membrane 9 has a thickness enabling transfer of mechanical vibration between the actuating/detecting element 4A, 4B and the resonating element 3, 3A, 3B, 3C, 3D.

4 Claims, 9 Drawing Sheets

DENSITY AND VISCOSITY SENSOR

FIELD OF THE INVENTION

The invention relates to a sensor for measuring density and viscosity of a fluid. The sensor is based on the use of mechanical elements put into vibration in the fluid to be measured.

The invention is applicable to density and viscosity measurements in the oilfield industry, in the chemical industry, in the food industry, etc. . . .

BACKGROUND OF THE INVENTION

The density is a measure of a mediums mass per unit of volume. The SI unit of density is the kilogram per cubic meter ($kg/m^3$). As examples, at standard temperature and pressure condition, the density of water is $1000 \, kg/m^3$, of ethyl alcohol is $790 \, kg/m^3$, respectively.

Viscosity is a measure of the resistance of a fluid to deformation under shear stress. Viscosity describes a fluid internal resistance to flow and may be thought of as a measure of fluid friction. The SI physical unit of dynamic viscosity is the Pascal second (Pa·s). The cgs physical unit for dynamic viscosity is the poise (P). It is more commonly expressed, particularly in ASTM standards, as centipoise (cP). As example, water has a viscosity of 1.0 cP (at 20° C.).

It is known from patent document EP0282251, a transducer for measuring density or viscosity of fluid. The transducer comprises two parallel tines extending from a common yoke, forming a tuning fork adapted to be immersed in the fluid. The tines are excited to vibrate resonantly and in antiphase by one or more piezoelectric exciting elements, which are housed in one or more cavities within the tines or the yoke. The vibrations are sensed by one or more similarly-housed piezoelectric sensing elements.

This transducer has a typical size of several centimeters requiring a bulky and expensive sensor housing. This leads to a highly intrusive measuring device preventing its use in small sample chambers or small pipes. Further, operation at high pressure and high temperature is also very difficult to implement due to the large size.

SUMMARY OF THE INVENTION

One goal of the invention is to propose a sensor for measuring density and viscosity of a fluid that overcomes at least one of the shortcomings of the prior art.

According to a first aspect of the invention, the excitation-detection scheme of the present sensor is based on the transfer of a mechanical signal through a membrane having on one side an actuating/detecting element isolated from the fluid and on the other side a resonating element immersed in the fluid. More precisely, the density and viscosity sensor of the invention comprises a resonating element arranged to be immersed in the fluid, an actuating/detecting element coupled to the resonating element, and a connector for coupling to the actuating/detecting element. The sensor further comprises a housing defining a chamber isolated from the fluid, the housing comprising an area of reduced thickness defining a membrane separating the chamber from the fluid. The actuating/detecting element is positioned within the chamber so as to be isolated from the fluid and mechanically coupled to the membrane. The resonating element arranged to be immersed in the fluid, is mechanically coupled to the membrane. The membrane has a thickness enabling pressure resistance and transfer of mechanical vibration between the actuating/detecting element and the resonating element. The resulting membrane stiffness enables decoupling the resonating element properties from the actuating/detecting element.

More precisely, the density and viscosity sensor according to the invention comprises a resonating element arranged to be immersed in the fluid, an actuating/detecting element coupled to the resonating element, and a connector for coupling to the actuating/detecting element. The sensor further comprises a housing defining a chamber isolated from the fluid, the housing comprising an area of reduced thickness defining a membrane separating the chamber from the fluid. The actuating/detecting element is positioned within the chamber so as to be isolated from the fluid and mechanically coupled to the membrane. The resonating element arranged to be immersed in the fluid is mechanically coupled to the membrane. The membrane has a thickness enabling transfer of mechanical vibration between the actuating/detecting element and the resonating element.

The resonating element may be mechanically coupled to the membrane by a mechanical coupling element.

The area of reduced thickness may form a cavity in which the actuating/detecting element is secured.

The actuating/detecting element may comprise at least one piezoelectric element. The piezoelectric element comprises a first and a second side, the first side being coupled to the connector by a connecting wire, the second side being electrically coupled to the membrane.

The piezoelectric element may be pushed against the membrane through a plug arrangement screwed into the cavity. The plug comprises a hole for coupling to the connecting wire.

The connector may be a coaxial connector comprising an external metallic part in contact with the housing and an internal metallic part coupled to the connecting wire, the external and internal metallic part being separated by an isolating part.

The sensor may further comprise a thermistance positioned within the chamber.

The sensor may comprise an electronic arrangement for driving the actuating/detecting element from an actuating mode into a detecting mode and vice-versa.

The resonating element comprises a first beam for measuring a first range of density and viscosity. It may further comprise at least a second beam for measuring a second range of density and viscosity. The resonating element may be chosen among the group of resonating elements comprising:

- a single part beam attached by sensibly its center to the coupling element,
- a single part beam attached by one end to the coupling element,
- a U-shaped beam comprising a first longitudinal part coupled to a second bent part attached by one end to the coupling element, and
- a double beam comprising a first beam and a second beam attached together, the first beam being attached to the coupling element.

Advantageously, the beam may comprise at least a wire aligned with the fluid flow direction.

According to a second aspect of the invention, the method for measuring density and viscosity of a fluid is based on a particular excitation-detection scheme. The excitation-detection scheme is based on an elementary sequence comprising three phases: an excitation phase, a waiting phase and a detection phase. During the excitation phase, an excitation signal of an initial frequency constituted by M periods is applied to the actuating/detecting element (for example M is equal to 4). The waiting phase has a duration of N periods (for example N is equal to 1). The detection phase has a duration of P periods (for example P is equal to 3). The elementary sequence is repeated K times (for example K is of the order of the quality factor Q) for the initial frequency, thus enabling the determination of a measured or actual in-phase spectral component and a measured or actual quadrature spectral component.

According to a first alternative, these steps are repeated for various frequencies between the initial frequency and the last frequency which encompass the resonating frequency of the resonating element. A measured or actual in-phase and quadrature spectrum are obtained.

According to a second alternative, these steps are repeated for various frequencies between the initial frequency and the last frequency which encompass the resonating frequency of the resonating element, and for two different values of the number of periods N (for example for N=1 and for N=4). The determination of a measured in-phase spectral component and a measured quadrature spectral component consists in calculating the difference between the in-phase spectral components obtained for the two different values of the number of periods N obtained. The same is done with the quadrature spectral components. A measured or actual in-phase and quadrature spectrum are obtained.

Subsequently, a parametrical identification is performed on the in-phase spectrum and the quadrature spectrum. The parametrical identification consists in comparing the measured spectrum relatively to theoretical spectrum calculated based on a plurality of discrete value of quality factor and resonant frequency pair. For each quality factor and resonant frequency pair, a first and a second intercorrelation coefficients are calculated for the in-phase spectrum and quadrature spectrum, respectively. The quality factor and resonant frequency pair corresponding to a maximum of the normalized sum of the first and second intercorrelation coefficients, determines the quality factor and resonant frequency of the resonating element in the fluid to be measured.

More precisely, the density and viscosity measuring method according to the invention comprises the steps of:
a) applying an excitation signal to a resonating arrangement comprising an actuating/detecting element and a resonating element arranged to be immersed in the fluid, the excitation signal having a first frequency,
b) detecting a reception signal provided by the resonating arrangement,
c) repeating the excitation signal applying step and the reception signal detecting step at various frequencies so that a range of frequencies is swept according to a frequency increment,
d) determining an in-phase sensor actual response and a quadrature sensor actual response based on the reception signal detected in the range of frequencies,
e) calculating an in-phase sensor model response and a quadrature sensor model response based on an initial resonant frequency and an initial quality factor of the resonating element,
f) comparing the in-phase sensor model response to the in-phase sensor actual response, and the quadrature sensor model response to the quadrature sensor actual response by determining an associated correlation coefficient,
g) repeating the calculating step and the comparing step with a modified resonant frequency and a modified quality factor and storing a determined number of resonant frequency, quality factor and associated correlation coefficient,
h) determining a resulting resonant frequency and a resulting quality factor of the resonating element in the fluid based on the determined number of associated correlation coefficient, and
i) determining density and viscosity of the fluid based on the resulting resonant frequency, the resulting quality factor and a sensibly exact analytical modelling of the resonating element.

The comparison and resonant frequency/quality factor determination steps may be based on parametrical identification consisting in:
calculating a normalized correlation coefficient sum for each sensor model response calculated for the determined number of resonant frequencies and quality factor of the resonating element, and
determining the resulting resonant frequency and the resulting quality factor corresponding to a resonant frequency/quality factor pair which is associated with the higher normalized correlation coefficient sum.

According to a first excitation scheme, the excitation signal has a determined frequency which is repeated a number of time, and the in-phase sensor actual response and the quadrature sensor actual response are determined based on an average of the reception signals for each frequency detected in the range of frequencies.

According to a second excitation scheme, the excitation signal comprises a first excitation signal and a second excitation signal, the first excitation signal having a first number of periods and the second excitation signal having a second number of periods. The excitation signals are repeated at various frequencies so that a range of frequencies is swept according to a frequency increment, a first reception signal being associated with the first excitation signal and a second reception signal being associated with the second excitation signal. The in-phase sensor actual response is determined based on a subtraction calculation between the in-phase sensor actual response associated with the first reception signal and the in-phase sensor actual response associated with the second reception signal. The quadrature sensor actual response is determined based on a subtraction calculation between quadrature sensor actual response with the first reception signal and the quadrature sensor actual response associated with the second reception signal.

Thus, according to the invention the excitation/detection elements are completely isolated from the fluid. As the parts of the sensor being immersed in the fluid being only the resonating element and a part of the housing, the sensor of the invention has a high chemical resistance, high pressure resistance and high temperature resistance.

The sensor design allows a minimal intrusion in the fluid flow line to be measured, thus avoiding fluid flow perturbations, erosion issues, potential plugging and ensuring sensor reliability over a long period of time.

Further, the actuation/detection part being decoupled form the resonating part, it allows a complete freedom in the choice of the resonating element material, irrespective of its electrical properties. In particular high corrosion resistant alloys or high strength crystals can be used.

Also, as there is no electrical feed-through between the resonating element and the actuating/detecting element, the sensor housing can be made of a simple and robust monolithic block. Thus, temperature induced stress effects are reduced. The sensor can be miniaturized with regards to prior art sensor and well adapted for harsh environment applications. It is also well adapted to be manufactured at low cost.

Finally, the measurement method of the invention allows a drastic reduction of the background offsets and noise. This greatly improves the operating range of the sensor and the density/viscosity predictions robustness and accuracy.

BRIEF DESCRIPTION OF THE DRAWINGS

The present invention is illustrated by way of examples and not limited to the accompanying figures, in which like references indicate similar elements:

FIG. 6.A is a cross-section view along line AA of FIG. 5 showing a sensor for measuring density and viscosity of a fluid according to a first embodiment of the invention;

FIG. 6.B is a cross-section view along line AA of FIG. 5 showing a sensor for measuring density and viscosity of a fluid according to an alternative of the first embodiment of the invention;

FIG. 6.C is a cross-section view along line AA of FIG. 5 showing a sensor for measuring density and viscosity of a fluid according to another alternative of the first embodiment of the invention;

FIGS. 7.A and 7.B are perspective views of a piezoelectric element according to a first and a second alternative, respectively;

FIGS. 8.A, 8.B and 8.C are side, bottom and perspective bottom views schematically showing a sensor for measuring density and viscosity of a fluid according to a second embodiment of the invention, respectively;

FIGS. 9.A, 9.B and 9.C are side, bottom and perspective bottom views schematically showing a sensor for measuring density and viscosity of a fluid according to a third embodiment of the invention, respectively;

FIGS. 10.A, 10.B and 10.C are side, bottom and perspective bottom views schematically showing a sensor for measuring density and viscosity of a fluid according to a fourth embodiment of the invention, respectively;

FIGS. 12.A and 12.B schematically illustrate the sensor excitation and detection scheme according to a first alternative and a second alternative, respectively;

FIGS. 17.A and 17.B are perspective and cross-section views schematically showing a sensor for measuring density and viscosity of a fluid coupled to a conduit according to a first alternative; and FIGS. 18.A and 18.B are perspective and cross-section views schematically showing a sensor for measuring density and viscosity of a fluid coupled to a conduit according to a second alternative.

DETAILED DESCRIPTION OF THE INVENTION

FIGS. 1 to 5 show the density and viscosity sensor 1 of the invention.

The density and viscosity sensor 1 comprises a housing 2. The housing 2 comprises a connector 7, for example a standardized coax connector. The housing 2 may comprise a groove 10 for an O-ring type sealing (not shown). The sealing separates a fluid contacting side FCS from the sensor connecting side SCS. The fluid contacting side may be submitted to harsh environment (high pressure, corrosive fluid . . . ). The connecting side is typically at the atmospheric pressure. The sensor comprises a resonating element 3A. The resonating element 3A is coupled to the housing 2 by a mechanical coupling element 5. In the embodiment illustrated in FIGS. 1 to 6B, the resonating element 3A is under the form of a single beam attached at its center to the housing 2 by the mechanical coupling element 5.

In this particular embodiment, the mechanical coupling element 5 constitutes an integral part with the housing. However, it will be apparent for a person skilled in the art that the mechanical coupling element 5 may constitute an integral part with the resonating element or may be an additional part coupled to the housing and to the resonating element. The function of the mechanical coupling element is to mechanically couple the housing 2 to the resonating element 3A so that vibration can be transmitted through it. Another function is to position the resonating element 3A into the fluid to be measured, so that the resonating element is surrounded by said fluid or totally immersed in said fluid. The resonating element 3A and the housing integral or not with the coupling element 5 may be assembled together (e.g. by any appropriate welding, gluing, brazing etc. technique).

Figure 1:
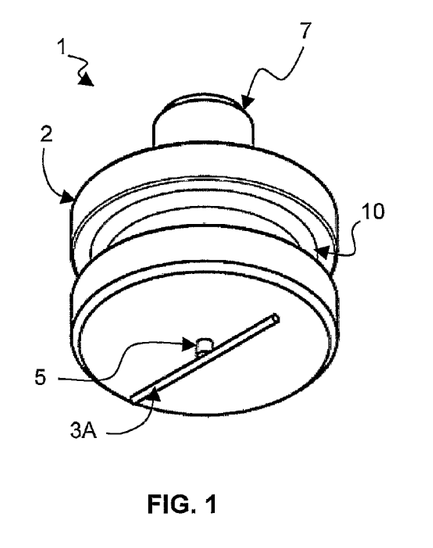
FIGS. 1, 2, 3, 4 and 5 are perspective bottom and top views, bottom, top and side views schematically showing a sensor for measuring density and viscosity of a fluid according to a first embodiment of the invention, respectively.
Figure 2:
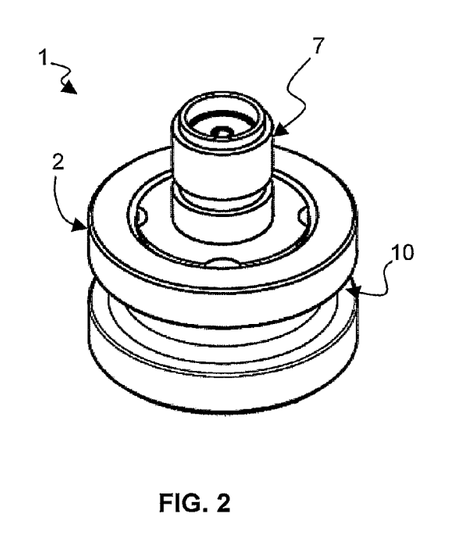
Figure 3:
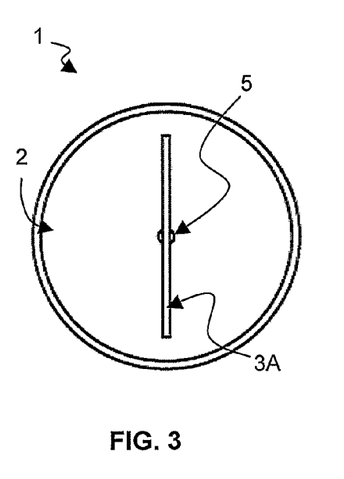
Figure 4:
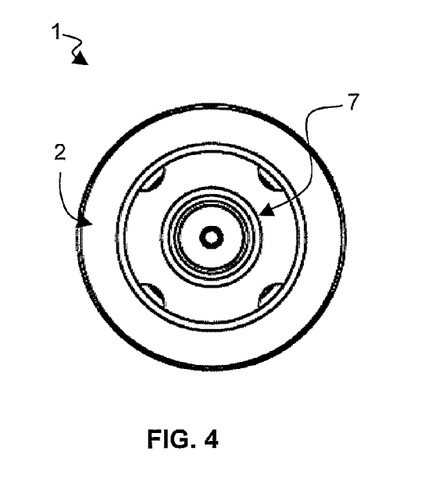
Figure 5:
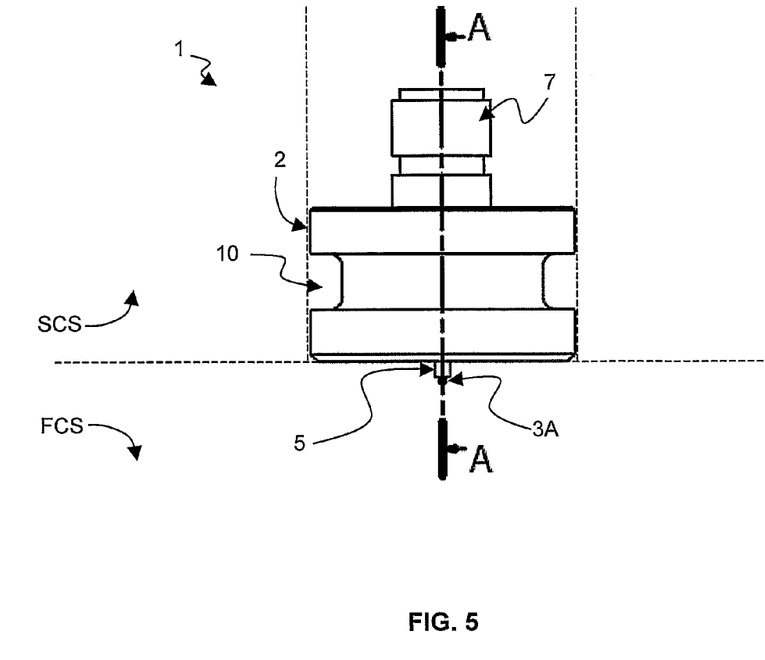
Figure 6:
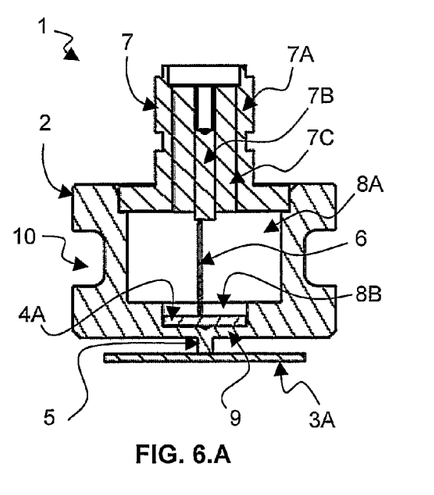

FIG. 6.A is a cross-section view in a sensor 1 according to a first alternative of the first embodiment. The housing comprises a housing interior part defining a chamber 8A. The housing 2, in the chamber side, comprises a cavity 8B. The cavity 8B defines an area where the housing has a reduced thickness defining a membrane 9 between the chamber 8A and the fluid contacting side FCS. The coupling element 5 is positioned onto the membrane 9. Preferably, the coupling element 5 is positioned at sensibly a center point on the membrane. The chamber 8A may be filled with a material. Advantageously, the material is a vibration absorbing material (e.g. gas, oil, gel, etc. . . . ). The vibration absorbing material enables to reduce perturbation due to parasitic vibration modes of the housing itself. The chamber 8A may be sealed via the connector 7.

An actuating/detecting element 4, for example a piezoelectric element 4A is positioned in the cavity 8B. One side of the piezoelectric element is coupled to the connector 7 by a connecting wire 6. The other side of the piezoelectric element 4A is electrically coupled to the membrane 9. In this alternative, the piezoelectric element is mainly working in extension.

Typically, a piezoelectric element comprises a metal layer substantially on its overall surface and on each side.

The electrical coupling may be obtained either by gluing the piezoelectric element onto the membrane via a conductive glue, or by a piezoelectric element mechanically secured against the membrane, or by brazing the piezoelectric element onto the membrane.

The connector 7 comprises an external metallic part 7A in contact with the housing 2 and an internal metallic part 7B. The external 7A and internal 7B metallic part are separated by an isolating part 7C. Thus, the piezoelectric element 4 may be excited by an appropriate electrical signal applied between its two sides, namely on the one side by the external metallic part 7A and the housing 2, and on the other side by the metallic part 7B and the connecting wire 6.

FIG. 6.B is a cross-section view in a sensor 1 according to a second alternative of the first embodiment. According to this alternative, a thermistance 11 is positioned within the chamber 8A of the housing. The thermistance enables a measurement of temperature at the position where the viscosity and density measurement are performed. Additionally, the thermistance 11 may be further connected to a resistance 12 for adapting the range of temperature measurement to the particular application for which the density and viscosity sensor is intended to be used. The temperature measurement may be useful to compensate for temperature effects on density and viscosity measurements. The thermistance is given as example, others temperature measuring arrangements may be used, e.g. a diode.

FIG. 6.C is a cross-section view in a sensor 1 according to a third alternative of the first embodiment of the invention. For clarity purpose, the connector 7 is omitted in FIG. 6C. According to this alternative, the sensor further comprises a plug 13 and a screwing plug 14 screwed into the chamber 8A or the cavity 8B for applying the piezoelectric element 4A onto the membrane 9. The screwing plug 14 comprises an appropriate hole for the passage of the connecting wire 6 at sensibly the screwing plug center. The plug 13 enables application of the piezoelectric element onto the membrane when the screwing plug 14 is screwed. The plug 13 lets a passage for the connecting wire 6 from the screwing plug center to the piezoelectric element. One side of the piezoelectric element is coupled to the connector (not shown) by the connecting wire 6. The other side of the piezoelectric element 4A contacts the membrane 9.

For clarity purpose, FIG. 6.C also shows a magnified portion of the piezoelectric element 4A area. The piezoelectric element 4A comprises two superposed piezoelectric elements 4A1 and 4A2 coupled to each other through a first conductive layer 6A. The first coupling layer 6A is connected to the connecting wire 6. The first piezoelectric element 4A1 is also coupled to the plug 13 by a second conductive layer 13A. The second piezoelectric element 4A2 is also coupled to the membrane 9 by a third conductive layer 9A. The first piezoelectric element 4A1 has an inversed polarization state relatively to the second piezoelectric element 4A2. In this alternative, the piezoelectric elements are mainly working in compression. Thus, the two superposed piezoelectric elements 4A1 and 4A2 may be excited by an appropriate electrical signal applied between on the one side the first conductive layer 6A, and on the other side the second and third conductive layers 9A, 13A.

Though not shown in the Figures, a stack of additional piezoelectric elements (e.g. 3, 4, 5, etc. . . . piezoelectric elements) with appropriate polarization and conductive layers connections can be made. Greater is the number of piezoelectric elements, the more signal is delivered by the stack, thus improving measurements that can be made with the sensor.

Advantageously, the sensor further comprises any appropriate means for securing the sensor to a conduit, a tube or a pipe (flange, screw connection, etc. . . . ). Two examples will be given hereinafter in relation with FIGS. 17 and 18.

Figure 7:
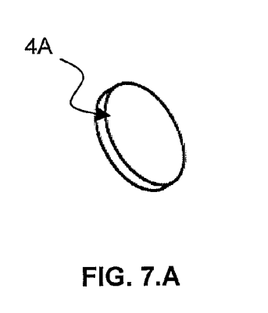

FIGS. 7.A and 7.B show an actuating/detecting element 4 under the form of a piezoelectric element. According to a first alternative shown in FIG. 7.A, the piezoelectric element has a plain cylindrical shape 4A. According to a second alternative shown in FIG. 7B, the piezoelectric element has a ring shape 4B, namely cylindrical shape that is hollow in its center part. Advantageously, the piezoelectric element according to the second shape withstands higher deformation than the first shape. Thus, the piezoelectric element breaking risk under important stress especially to high pressure is greatly reduced. More precisely, the piezoelectric element is submitted to extension stress at the center part and compression at the rand. The extension stress may lead to piezoelectric element breakage.

Figure 8:
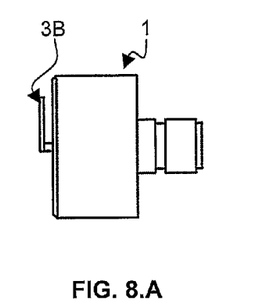

FIGS. 8.A, 8.B and 8.C are side, bottom and perspective bottom views schematically showing a density and viscosity sensor 1 according to a second embodiment of the invention, respectively.

According to this embodiment the resonating element 3B is under the form of a single part beam attached at one end of the beam to the coupling element 5.

Figure 9:
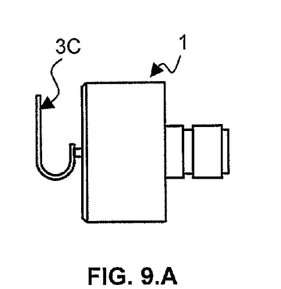

FIGS. 9.A, 9.B and 9.C are side, bottom and perspective bottom views schematically showing a density and viscosity sensor 1 according to a third embodiment of the invention, respectively.

According to this embodiment the resonating element 3C is under the form of a non-symmetrical U beam. The beam may be a wire having e.g. a cylindrical cross-section or an elliptical cross-section and a diameter of a few micrometers. The wire comprises a first longitudinal part contacting the fluid to be measured. The wire comprises a second bent part which is attached by one end to the coupling element 5.

Preferably, the beam according to the first, the second and the third embodiment is aligned with the fluid flow. This configuration enables to minimize erosion effect in high velocity particles fluid. It also enables to minimize turbulences induced by the presence of the measuring device and thus the noise on the beam.

Figure 10:
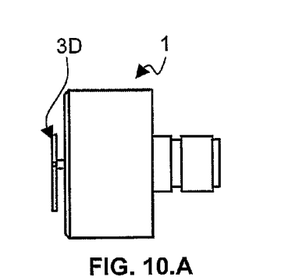

FIGS. 10A, 10.B and 10.C are side, bottom and perspective bottom views schematically showing a density and viscosity sensor 1 according to a fourth embodiment of the invention, respectively.

According to this embodiment the resonating element 3D comprises a first beam 301 and a second beam 302. Each wire is immersed in the fluid to be measured. The first beam 301 is attached by one of its point to the coupling element 5. The second beam 302 is attached by one of its point to the first beam. The first beam may be positioned relatively to the second beam according to any angle, preferably 90°. The point of attachment of the first beam may be chosen in the middle of the wire so that symmetrical beam may be formed or at any point of the wire so that dissymmetrical beam may be formed. The same is true for the second beam. Combination of symmetrical beam and dissymmetrical beam are also possible.

Advantageously, each beam has its own quality factor and resonant frequency. Thus, the multiple beams of different lengths offer an extended density and viscosity measurement range (each beam being sensible to a particular density and viscosity range). The multiple beams of same length improve the signal to noise ratio, thus improving the sensor accuracy.

In the hereinbefore described embodiments, the various beams that can be seen in the Figures comprise wires having a circular cross-section. However, this is not limitative as the beams may alternatively comprise any wire having an elliptical cross-section or having a parallelepipedic cross-section (for example a rectangular cross-section) or having a triangular cross-section, etc. . . . The diameter or the width of the wire may be a few hundreds of micrometers.

Advantageously, the sensor housing is made of high strength and high corrosion resistance stainless steel, for example Inconel.

Advantageously, the resonating element is made of high strength and high corrosion resistance material, for example stainless steel or material with low density such as sapphire or boron carbon. The use of sapphire or boron carbon improves sensitivity to fluid density.

Alternatively, the resonating element can be made of specific materials for detecting or measuring chemical species in the fluid.

Figure 11:
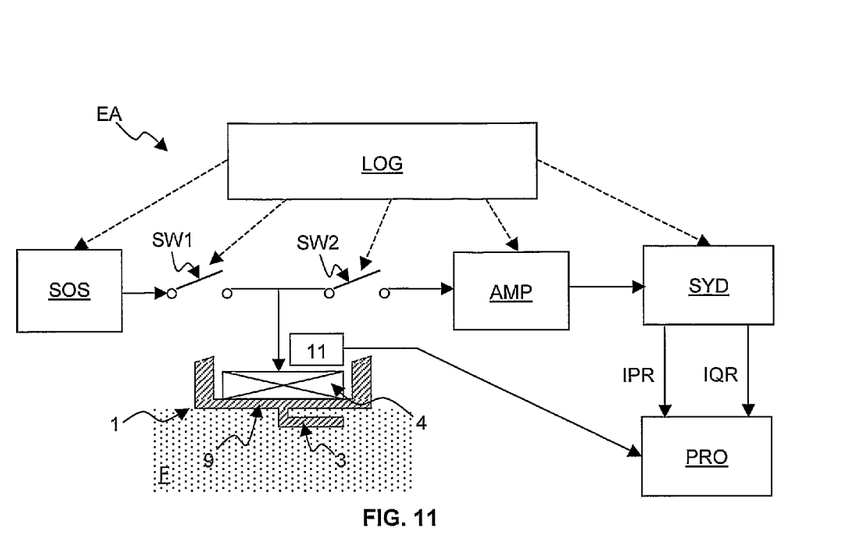
FIG. 11 schematically illustrates an electronic arrangement associated with the sensor of the invention.

FIG. 11 schematically illustrates an electronic arrangement EA associated with the density and viscosity sensor 1 of the invention. The electronic arrangement may form an integral part with the density and viscosity sensor 1 by integration inside the chamber, or may be externally coupled to the connector 7. The electronic arrangement may comprise discrete electronic components or may be implemented under the form of an integrated circuit.

The electronic arrangement EA comprises a controlling circuit LOG, an oscillator SOS, a first switch SW1, a second switch SW2, an amplifier AMP, a detection circuit SYS and a processing circuit PRO.

The controlling circuit LOG is coupled to the oscillator SOS, the first SW1 and second SW2 switch, the amplifier AMP and the detection circuit SYS.

Figure 12:
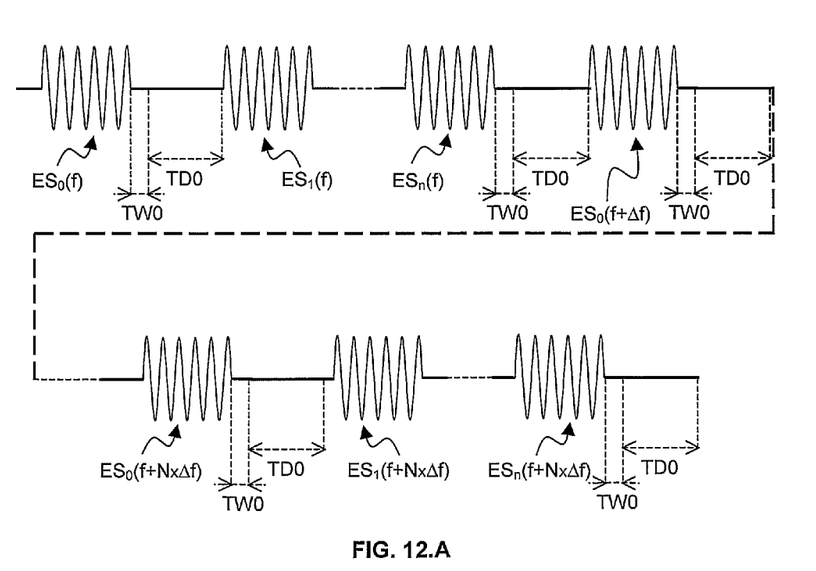

The oscillator SOS may be a sweep oscillator. The oscillator performs a sensor excitation and detection scheme that will be described in more details hereinafter (see FIGS. 12.A and 12.B).

In a first step, the controlling circuit LOG closes the first switch SW1 and opens the second switch SW2. Thus, the oscillator SOS applies an excitation signal to the piezoelectric element 4. The excitation signal application causes the piezoelectric element 4 to apply and relax strain to the membrane 9 and to the resonating element 3 by virtue of their mutual mechanical coupling. The excitation signal is typically in the Volt order.

Once a vibration has been established by exciting the piezoelectric element 3, the excitation could be removed and a reception signal representative of the vibration of the resonating element 3 in the fluid F can be measured. The reception signal is typically in the micro-Ampere order.

Accordingly, in a second step, the controlling circuit LOG closes the second switch SW2 and opens the first switch SW1. Thus, the piezoelectric element generates a reception signal representative of strain variation of the membrane 9 mechanically coupled to the resonating element 3.

The detection signal is amplified by the amplifier AMP. The detection circuit SYS performs a synchronous detection during a detection phase. It provides to the processing circuit PRO, an actual in-phase response signal IPR and an actual quadrature response signal IQR measured by the sensor 1.

The processing circuit PRO may also be connected to the thermistance 11. It provides a temperature measurement at the sensor level. The processing circuit PRO provides the density and viscosity of the fluid F according to a density and viscosity determination method that will be described in more details hereinafter (see FIG. 14).

It is to be noted that the second switch SW2 may be omitted or replaced by an appropriate resistance. The second switch SW2 basic function is to protect the amplifier AMP because of the difference of magnitude order between the excitation signal and the reception signal.

A first alternative of the density and viscosity sensor excitation and detection scheme is illustrated in FIG. 12.A. The excitation and detection scheme is based on the succession of an excitation phase followed by a waiting phase and a detection phase. In the first step, as described hereinbefore, a first excitation signal $ES_0(f)$ is applied to the piezoelectric element. The first excitation signal $ES_0(f)$ has a first frequency f and comprises a certain number of periods M (e.g. four periods, six periods, etc. . . . ). Then, in the second step, as described hereinbefore, after a waiting duration TW0, detection of the reception signal generated by the piezoelectric element takes place during a detection duration TD0. The waiting duration TW0 has a certain number of periods L, for example L is approximately one period and enables the system to relax before measurement is made. During the duration TD0, a decaying signal (not shown) due to the oscillation amortization of the resonating element in the fluid is measured. The detection duration TD0 has a certain number of period P, for example P is approximately three periods.

These two steps are repeated $n^{th}$ time, from an excitation signal $ES_1(f)$ to an excitation signal $ES_n(f)$. For example n=10, 50, 100, etc. . . .

Advantageously, n is sensibly equal to the quality factor Q of the resonating element. This choice enables a stabilized oscillating state to take place.

The above steps are then repeated so that the oscillator SOS provides an excitation signal which frequency sweeps a range of frequency encompassing the resonance frequency of the resonating element. More precisely, the above steps are repeated with a second excitation signal $ES_0(f+\Delta f)$. The second excitation signal $ES_0(f+\Delta f)$ has a second frequency $f+\Delta f$, corresponding to the first frequency f shifted by a frequency increment $\Delta f$. It comprises, the same number of periods as the first excitation signal $ES_0(f)$. These steps are repeated until the range of frequency is totally swept, namely until an excitation signal $ES_n(f+N\times\Delta f)$ and corresponding detection have been performed.

As an example, the oscillator SOS may sweep the frequency range between 8200 Hz and 8300 Hz with a frequency increment of 1 Hz and N=100.

For this alternative of excitation and detection scheme, the detected decaying signal is amplified. Then a synchronous detection is performed by the detection circuit. The detected decaying signal is multiplied to a signal of the sinus type and to a signal of the cosinus type, respectively. An average of the n signals for each frequency is performed. The multiplication to the sinus signal gives the in-phase response signal. The multiplication to the cosinus signal gives the quadrature response signal. The typical spectrum obtained will be described in details hereinafter in relation with FIGS. 15 and 16.

A second alternative of the density and viscosity sensor excitation and detection scheme is illustrated in FIG. 12.B. The excitation and detection scheme is based on the succession of an excitation phase followed by a waiting phase and a detection phase. In the first step, as described hereinbefore, a first excitation signal $ES'_0(f)$ is applied to the piezoelectric element. The first excitation signal $ES_0(f)$ has a first frequency f and comprises a certain number of periods M', at least two periods (e.g. four periods, six periods, etc. . . . ). Then, in the second step, as described hereinbefore, after a waiting duration TW0, detection of the reception signal generated by the piezoelectric element takes place during a duration TD0. The waiting duration TW0 lasts a certain number of period L', for example L' is approximately one period and enables the system to relax before measurement is made. During the duration TD0, a decaying signal (not shown) due to the oscillation amortization of the resonating element in the fluid is measured. The detection duration TD0 lasts a certain number of period P', for example P' is approximately three periods.

These two steps are repeated $n^{th}$ time, from an excitation signal $ES'_0(f)$ to an excitation signal $ES_n(f)$. For example n=10, 50, 100, etc. . . .

The above steps are then repeated so that the oscillator SOS provides an excitation signal which frequency sweeps a range of frequency encompassing the resonant frequency of the resonating element. More precisely, the above steps are repeated with a second excitation signal $ES'_1(f+\Delta f)$. The second excitation signal $ES'_1(f+\Delta f)$ has a second frequency f+$\Delta$f), corresponding to the first frequency f shifted by a frequency increment $\Delta f$. It comprises, the same number of periods as the first excitation signal $ES'_0(f)$. These steps are repeated until the range of frequency is totally swept, namely until an excitation signal $ES'n(f+n\times\Delta f)$ and corresponding detection have been performed.

As an example, the oscillator SOS may sweep the frequency range between 8200 Hz and 8300 Hz with a frequency increment of 1 Hz and n=100.

Subsequently, in an analogous manner, these steps are repeated for others excitation signals $ES''_0(f)$ to $ES''_n(f+n\times\Delta f)$, so that a range of frequency encompassing the resonance frequency of the resonating element is swept. The excitation signal $ES''_0(f), ES''_1(f+\Delta f, ES''_2(f+2\times\Delta f), \ldots, ES''n(f+n\times\Delta f)$ comprises only one period.

For this alternative of excitation and detection scheme, the detected decaying signal is amplified. Then a synchronous detection is performed by the detection circuit. The detected decaying signal is multiplied to a signal of the sinus type and to a signal of the cosinus type, respectively. The multiplication to the sinus signal gives the in-phase response signal. The multiplication to the cosinus signal gives the quadrature response signal. For a given frequency, the in-phase response resulting from the first excitation signal (at least two periods) is subtracted from the in-phase response resulting from the second excitation signal (only one period). Additionally, the quadrature response resulting from the first excitation signal (at least two periods) is subtracted from the quadrature response resulting from the second excitation signal (only one period). Thus, the results of the subtractions are corrected, at least partially, from the effects due to the sensor relaxation after the excitation period and not completely disappeared after the waiting period.

The typical spectrum obtained will be described in details hereinafter in relation with FIGS. 15 and 16.

Advantageously, for the first and second excitation and detection scheme hereinbefore described, the excitation signal finishes when the excitation signal is zero. This improves relaxation during the waiting phase.

Figure 13:
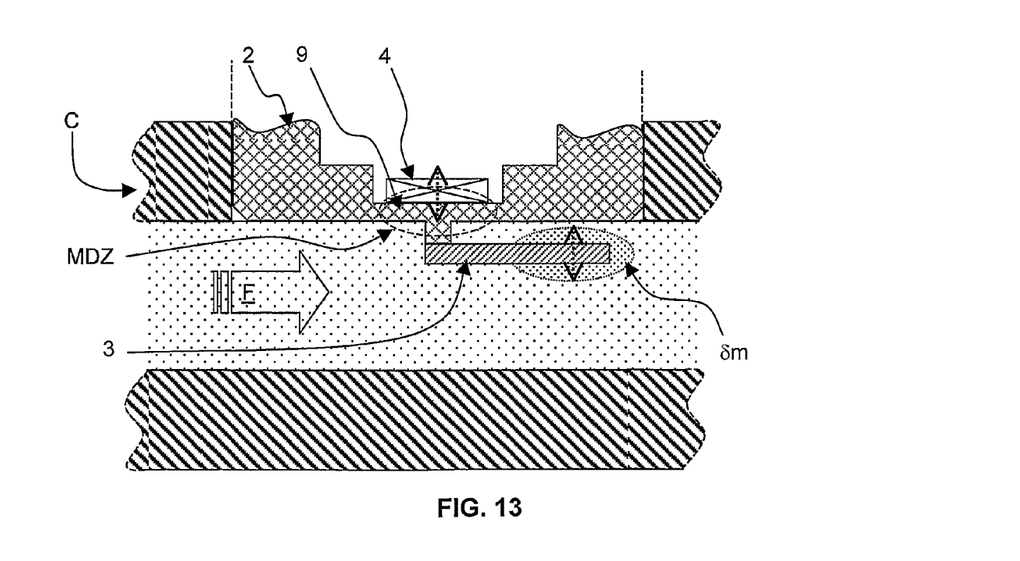
FIG. 13 is a cross-section view showing a sensor for measuring density and viscosity of a fluid fitted into a conduit and illustrating the measurement principle according to the invention.

FIG. 13 is a cross-section view showing a sensor 1 for measuring density and viscosity of fluid F fitted into a conduit C and illustrating the measurement principle according to the invention.

As the resonating element 3 vibrates in the fluid F, some of the surrounding fluid is displaced. The effective mass of the resonating element 3 is increased by an amount $\delta m$ determined by the volume of fluid entrained by the moving section. Consequently, this effect is related to fluid density, and a densitometer is provided.

As the resonating element 3 vibrates in the fluid F, the resonating element drags through the fluid in shear. Consequently, the vibration is dependent upon the resistance to shear of the fluid, and a viscometer is provided.

It is possible to sensibly determine an exact analytical modelling of the resonating element to fluid interaction (e.g. beams of first, second, third and fourth embodiments). For example, the interaction of the resonating element according to the second embodiment under the form of a single part beam having a circular cross-section (FIG. 8) into the fluid may be sensibly exactly modeled.

Firstly, based on the Navier Stockes equation:

$$\rho\frac{d\vec{v}}{dt} = -\overrightarrow{grad}P + \eta\Delta\vec{v} + \left(\xi + \frac{\eta}{3}\right)\overrightarrow{grad}(div\vec{v})$$

where $\rho$ corresponds to the fluid density, $$\overrightarrow{gradP}$$

represents the force coming from the pressure P, $\vec{v}$ corresponds to the vibrating speed of the beam, $\eta$ is the fluid viscosity and $\xi$ is the second fluid viscosity.

Secondly, based on true assumption that the fluid is a non-compressible fluid, the speed of the beam is low, the size of the beam is larger than the amplitude of the oscillation of the resonating element, and the added mass $\delta m$ is small compared to the beam mass, it can be calculated that:

The added mass on the beam is given by $\delta m=\pi\rho R^2$ where R represents the radius of the beam section.

The quality factor is given by $$Q = (\rho_{beam} + \rho_{fluid})\frac{R\delta\omega}{4\eta}$$

with $\rho_{fluid}$ corresponds to the fluid density.

The fluid viscosity is given by $$\eta = \frac{(\rho_{beam} + \rho_{fluid})^2\omega_0 R^2}{8\rho_{fluid}}\left(\frac{1}{Q} - \frac{\rho_{beam}}{(\rho_{beam} + \rho_{fluid})}\frac{1}{\omega_0}\frac{\omega_{vac}}{Q_{vac}}\right)^2$$

where $\omega_0$ is linked to beam resonance frequency into the fluid, and $\omega_{vac}$ is linked to beam resonance frequency into the vacuum and $Q_{vac}$ represents loss in the vacuum.

Figure 14:
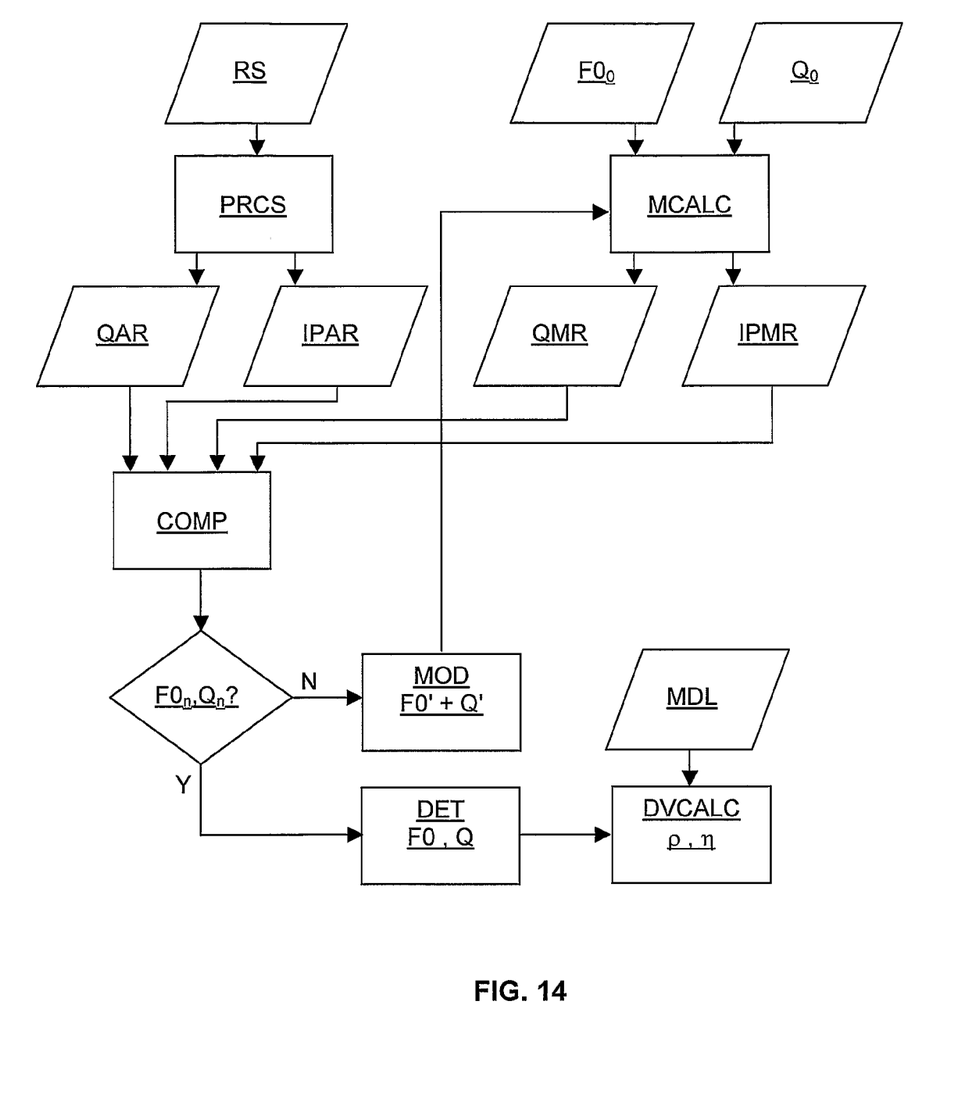
FIG. 14 is a diagrammatic illustration of a method for measuring density and viscosity of a fluid according to the invention.

FIG. 14 is a diagrammatic illustration of a method for measuring density and viscosity of fluid according to the invention.

In a first step, the resonating arrangement comprising the actuating/detecting element 4 and the resonating element 3, 3A, 3B, 3C, 3D arranged to be immersed in the fluid is excited according to the excitation and detection scheme described hereinbefore in relation with FIG. 12.A or 12.B.

In a second step, the reception signal RS provided by the resonating arrangement is detected. These two steps are repeated at various frequencies modified so that a range of frequencies is swept by successive frequency incrementing.

The various reception signal detected in the range of frequencies are processed PRCS and an in-phase sensor actual response spectrum (IPAR) and a quadrature sensor actual response spectrum (QAR) are determined.

Simultaneously, based on an initial resonant frequency $F0_0$ and an initial quality factor $Q_0$ of the resonating element, an in-phase sensor model response spectrum (IPMR) and a quadrature sensor model response spectrum (QMR) are calculated MCALC. Subsequently, the quadrature sensor model response (QMR) is compared COMP to the quadrature sensor actual response (QAR), and the in-phase sensor model response (IPMR) is compared COMP to the in-phase sensor actual response (IPAR).

The calculating step MCALC and the comparing step COMP are repeated with a modified MOD resonant frequency F0' and a modified quality factor Q' until the last values of the resonant frequency $F0_n$ and quality factor $Q_n$ are attained. Thus, a certain number of discrete values for the resonant frequency F0 and quality factor Q, preferably encompassing the values to be determined are swept.

Advantageously, the comparison step COMP between model response and actual response is based on parametrical identification. More precisely, a certain number of model responses are calculated for various resonant frequencies and various quality factors. The in-phase model responses are multiplied to the in-phase actual response point by point and a first intercorrelation coefficient is calculated for each model responses. The quadrature model responses are multiplied to the quadrature actual response point by point and a second intercorrelation coefficient is calculated for each model responses. The calculation of intercorrelation coefficient is a known mathematical calculation that will not be further explained.

The normalized correlation coefficient cc for a particular quality factor Q' and a particular resonant frequency $F_0'$ is given by the following formula:

$$cc = \frac{\sum_i s(f_i) \cdot S(Q', F_0', f_i) + \sum_i c(f_i) \cdot C(Q', F_0', f_i)}{\sqrt{\sum_i (S^2 + C^2)}},$$

where $s(f_i)$ is the measured in-phase spectrum for frequency $f_i$, $c(f_i)$ is the measured quadrature spectrum for frequency $f_i$, $S(Q', F_0', f_i)$ is the model in-phase spectrum for the frequency $f_i$, $C(Q', F_0', f_i)$ is the model quadrature spectrum for frequency $f_i$, the frequency $f_i$ sweeping the frequency range encompassing the resonant frequency.

For each resonant frequency/quality factor pair, the normalized correlation coefficient is calculated.

The resonant frequency F0 and the quality factor Q of the resonating element in the fluid are considered as determined DET for a resonant frequency/quality factor pair corresponding to the higher normalized sum. Obviously, the accuracy of determination of the resonant frequency/quality factor pair depends on the number of pairs used for calculating model responses, thus on the increment on the resonant frequency (for example 0.1 Hz) and on the quality factor (for example 1 unit).

In order to reduce the number of calculation while maintaining a good accuracy on the resonant frequency and on the quality factor determination, it is possible to limit the calculation of model responses to a limited potential number of quality factor and an increment on resonant frequency important (e.g. 10 Hz). For the best correlated pair, the correlation coefficient for adjacent pairs is also calculated (for example 8 pairs around the best correlated pair). Subsequently, an interpolation in two-dimension is performed in order to determine the best resonant frequency/quality factor pair (this is a known mathematical calculation that will not be further explained).

It is also possible to reduce the number of calculation by selectively comparing only the in-phase responses or only the quadrature responses.

Finally, the density η and viscosity ρ of the fluid can be calculated DVCALC based on the determined resonant frequency F0 and resulting quality factor Q and on a sensibly exact analytical modelling MDL of the resonating element to fluid interaction.

Figure 15:
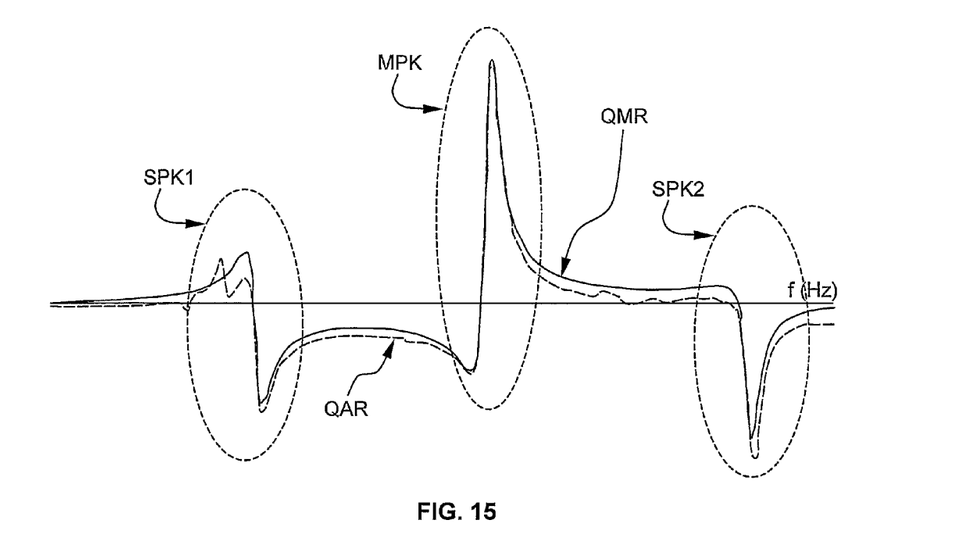
FIG. 15 shows a quadrature sensor actual response spectrum based on measurements and a quadrature model response spectrum based on calculation.
Figure 16:
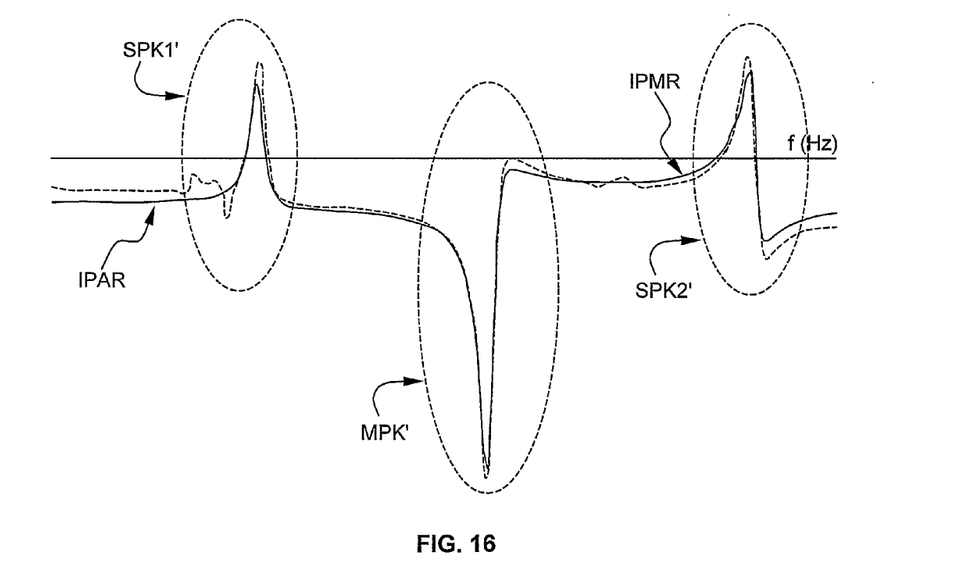
FIG. 16 shows an in phase sensor actual response spectrum based on measurements and an in phase model response spectrum based on calculation.

FIGS. 15 and 16 illustrate typical sensor response spectrum measured compared to response spectrum.

FIG. 15 shows a quadrature sensor actual response spectrum QAR and a quadrature model response spectrum QMR. These quadrature spectra comprise a main band peaks part MPK and a first SPK1 and a second SPK2 side bands peaks parts. The various peaks MPK, SPK1, SPK2, MPK', SPK1' and SPK2' are generated by the discontinuous excitation sequence of the actuating/detecting element and resonating element.

FIG. 16 shows an in phase sensor actual response spectrum IPAR and an in phase model response spectrum IPMR. These quadrature spectra comprise a main band peaks part MPK' and a first SPK1' and a second SPK2' side bands peaks parts.

The actual response spectrum QAR and IPAR are based on measurements made with the density and viscosity sensor of the invention. The model response spectrum QMR and IPMR are based on calculation. The fitting model includes the particular features of the resonating element of the density and viscosity sensor with which the measurements are made.

Based on the determined resonant frequency F0 and the quality factor Q and the fitting model for the particular resonating element used, the density η and viscosity ρ can be calculated. Preferably, the density and viscosity of the fluid can be further corrected based on temperature measurement made by, for example, the thermistance.

All the above measuring method steps are preferably implemented by the processing circuit PRO of the electronic arrangement EA.

Figure 17:
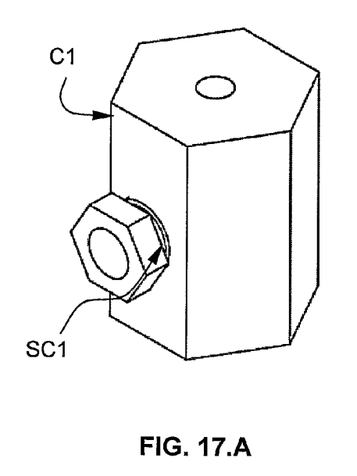

FIGS. 17.A and 17.B are perspective and cross-section views schematically showing a first example of the density and viscosity sensor 1 coupled to a hexagonal cross-section conduit part C1. The conduit part C1 comprises a connection CC1 for coupling to a main conduit or pipe. The density and viscosity sensor 1 is fitted into a threaded housing SC1. The hexagonal cross-section conduit part C1 comprises a threaded hole for screwing to the threaded housing SC1. The threaded hole comprises an abutment so that, when the threaded housing SC1 is screwed, the resonating element is optimally positioned within the conduit part C1.

Figure 18:
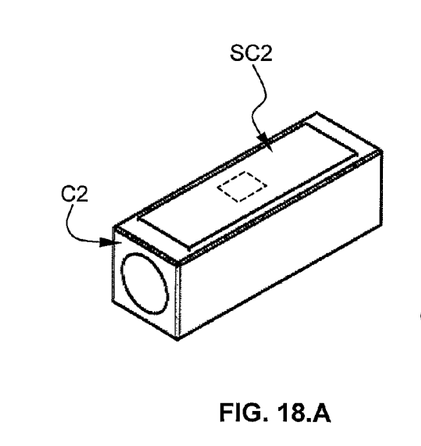

FIGS. 18.A and 18.B are perspective and cross-section views schematically showing a first example of the density and viscosity sensor 1 coupled to a rectangular cross-section conduit part C2. The conduit part C2 comprises a connection CC2 for coupling to a main conduit or pipe. The density and viscosity sensor 1 is fitted into a receiving part of a connecting housing SC2. The connecting housing SC2 also comprises a plate. The rectangular cross-section conduit part C2 comprises a hole for insertion of the receiving part. When the connecting housing SC2 is inserted into the hole, the plate comes in abutment onto the external part of the conduit. Thus, the resonating element is optimally positioned within the conduit part C1. The plate is coupled to the external part of the conduit according to any appropriate assembling technique.

Final Remarks

An actuating/detecting element under the form of a piezoelectric element has been described. However, it will be apparent that this is an example of actuating/detecting element and that any electrical/mechanical vibration converting arrangement, e.g. a electrical motor, may be employed.

It will be apparent for a person skilled in the art, that the invention is not limited to the four particular resonating elements described hereinbefore. Provided that one can find the equation modeling the behavior of the resonating element 3 in a fluid, said element may have others shapes, for example a spherical mass at one end of a beam, a beam stretched between the two arms of a fork, etc. . . .

It will also be apparent for a person skilled in the art, that the number of beams constituting the resonating element is not limited to one or two as described in the fourth embodiments. A plurality of beam may be coupled to the membrane, each beam having its own resonating frequency and thus enabling to measure a particular density and viscosity range.

Further, the beams are shown in the Figures as sensibly parallel to the area of the sensor housing contacting the fluid to be measured. However, it will be apparent for a person skilled in the art that each beam may be positioned relatively to the area of the sensor housing contacting the fluid to be measured according to any angle (for example 10°, 30°, 45°, etc. . . . ).

The connection of the density and viscosity sensor to a conduit in which flow a fluid to be measured is not limited to the two examples hereinbefore described. It will be apparent for a person skilled in the art that others connections are possible depending of the application of the density and viscosity sensor.

Also, the meaning of the term "connector" used in hereinbefore is not limited to a mechanical/electrical connection. It will be apparent for a person skilled in the art that a wireless connector may be used to transmit measurements from the sensor to any system requiring such measurements.

The invention finds application in various industry domains, for example the oilfield industry as density and viscosity sensor in down-hole tool, the chemical industry (plastic manufacturing, cosmetic preparation manufacturing), food industry, etc. . . . It may also be employed in aeronautical applications, for example for detecting the formation of ice on e.g. plane wing by measuring the shift of resonance frequency due to the ice added mass on the resonating element.

The drawings and their description hereinbefore illustrate rather than limit the invention. Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. A method for measuring density and viscosity of a fluid comprising the steps of:
   a) applying an excitation signal to a resonating arrangement comprising an actuating/detecting element and a resonating element arranged to be immersed in the fluid (F), the excitation signal having a first frequency (f),
   b) detecting a reception signal provided by the resonating arrangement,
   c) repeating the excitation signal applying step and the reception signal detecting step at various frequencies so that a range of frequencies is swept according to a frequency increment ($\Delta f$),
   d) determining an in-phase sensor actual response and a quadrature sensor actual response based on the reception signal detected in the range of frequencies,
   wherein the method further comprises the steps of:
   e) calculating an in-phase sensor model response and a quadrature sensor model response based on an initial resonant frequency and an initial quality factor of the resonating element,
   f) comparing the in-phase sensor model response to the in-phase sensor actual response, and the quadrature sensor model response to the quadrature sensor actual response by determining an associated correlation coefficient,
   g) repeating the calculating step and the comparing step with a modified resonant frequency and a modified quality factor and storing a determined number (n) of resonant frequencies, quality factors and associated correlation coefficients,
   h) determining a resulting resonant frequency and a resulting quality factor of the resonating element in the fluid (F) based on the determined number (n) of associated correlation coefficient, and
   i) determining density and viscosity of the fluid (F) based on the resulting resonant frequency, the resulting quality factor and a sensibly exact analytical modelling of the resonating element.

2. A density and viscosity measuring method according to claim 1, wherein the comparison and resonant frequency/quality factor determination steps are based on parametrical identification comprising:
   calculating a normalized correlation coefficient sum for each sensor model response calculated for the determined number (n) of resonant frequencies and quality factor of the resonating element, and
   determining the resulting resonant frequency and the resulting quality factor corresponding to a resonant frequency/quality factor pair which is associated with the higher normalized correlation coefficient sum.

3. A density and viscosity measuring method according to claim 2, wherein:
   the excitation signal has a determined frequency (f, f+$\Delta$f, . . . , f+N×$\Delta$f) repeated a number of times (n), and
   the in-phase sensor actual response and the quadrature sensor actual response are determined based on an average of the reception signals for each frequency detected in the range of frequencies.

4. A density and viscosity measuring method according to claim 1, wherein:
   the excitation signal comprises a first excitation signal and a second excitation signal, the first excitation signal having a first number of periods and the second excitation signal having a second number of periods, said excitation signals being repeated at various frequencies so that a range of frequencies is swept according to a frequency increment ($\Delta f$), a first reception signal is associated with the first excitation signal and a second reception signal is associated with the second excitation signal,
   the in-phase sensor actual response is determined based on a subtraction calculation between the in-phase sensor actual response associated with the first reception signal and the in-phase sensor actual response associated with the second reception signal, and
   the quadrature sensor actual response is determined based on a subtraction calculation between quadrature sensor actual response with the first reception signal and the quadrature sensor actual response associated with the second reception signal.

* * * * *